United States Patent
Khalaj

(10) Patent No.: US 8,979,805 B1
(45) Date of Patent: Mar. 17, 2015

(54) CATHETER CONNECTOR SECUREMENT DEVICE

(71) Applicant: Kimberly-Clark Worldwide, Inc., Neenah, WI (US)

(72) Inventor: Steve Saeed Khalaj, Laguna Hills, CA (US)

(73) Assignee: Avent, Inc., Alpharetta, GA (US)

( * ) Notice: Subject to any disclaimer, the term of this patent is extended or adjusted under 35 U.S.C. 154(b) by 0 days.

(21) Appl. No.: 14/089,870

(22) Filed: Nov. 26, 2013

(51) Int. Cl.
*A61M 25/02* (2006.01)

(52) U.S. Cl.
CPC ....... *A61M 25/02* (2013.01); *A61M 2025/0246* (2013.01); *A61M 2025/0266* (2013.01)
USPC .......................................... 604/174; 604/180

(58) Field of Classification Search
CPC . A61M 25/01; A61M 25/02; A61M 2025/01; A61M 2025/02; A61M 2025/0206; A61M 25/0213; A61M 2025/0266; A61M 2025/024
USPC ........... 604/165.03, 174, 178, 179, 180, 181, 604/250, 533
See application file for complete search history.

(56) References Cited

U.S. PATENT DOCUMENTS

| 7,014,627 | B2 | 3/2006 | Bierman | |
|---|---|---|---|---|
| 7,635,355 | B2 | 12/2009 | Bierman | |
| 7,959,623 | B2 | 6/2011 | Massengale | |
| 8,394,065 | B2 | 3/2013 | Bierman | |
| 2002/0133121 | A1* | 9/2002 | Bierman | 604/174 |
| 2009/0184026 | A1 | 7/2009 | Massengale et al. | |
| 2011/0288487 | A1* | 11/2011 | Wright et al. | 604/174 |
| 2012/0041423 | A1* | 2/2012 | Racz et al. | 604/533 |

FOREIGN PATENT DOCUMENTS

CA           2 495 013        2/2004

* cited by examiner

*Primary Examiner* — Theodore Stigell
*Assistant Examiner* — Amber Stiles
(74) *Attorney, Agent, or Firm* — Dority & Manning, P.A.

(57) ABSTRACT

A catheter connector and securement device system includes a connector seated within a securement device. The securement device includes a lower shell member having a perimeter wall defining an interior cradle space that conforms to the connector body. A cover member is hinged to the lower shell member at a hinge line and is movable from an open position for insertion and removal of the connector to a closed position wherein the cover member releasably latches to the lower shell member to retain the connector within the lower shell member. A catheter retention device may be spaced from the perimeter wall.

16 Claims, 4 Drawing Sheets

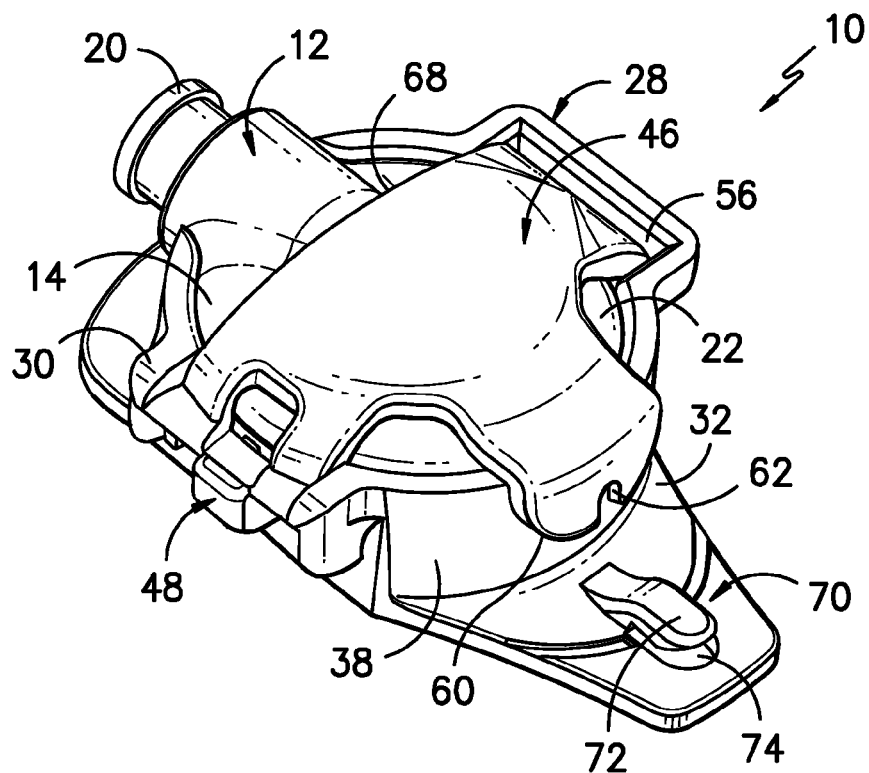
FIG. -1-
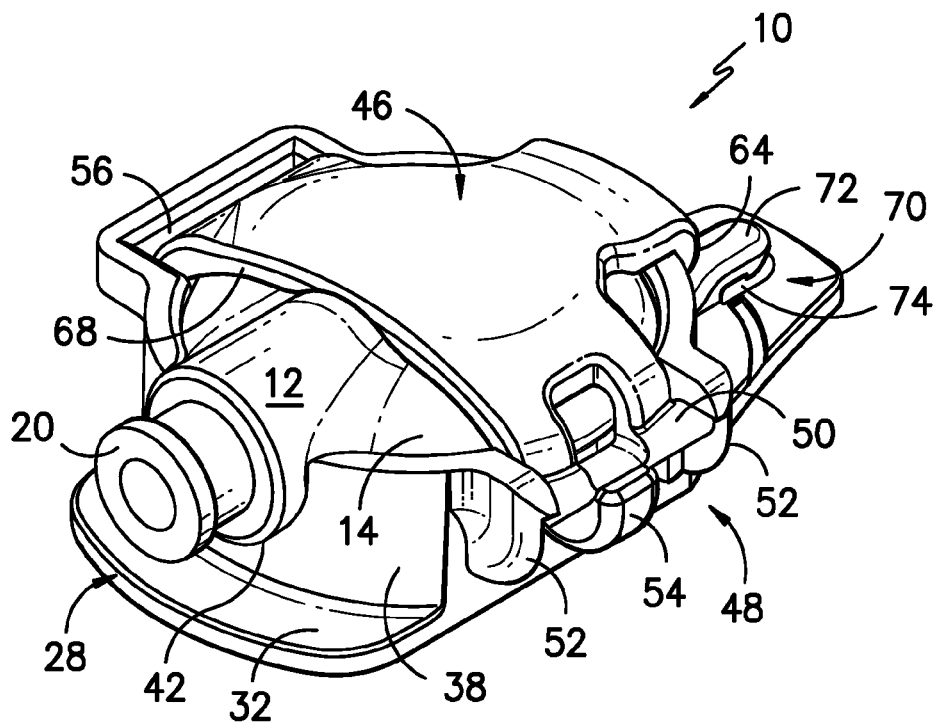
FIG. -2-

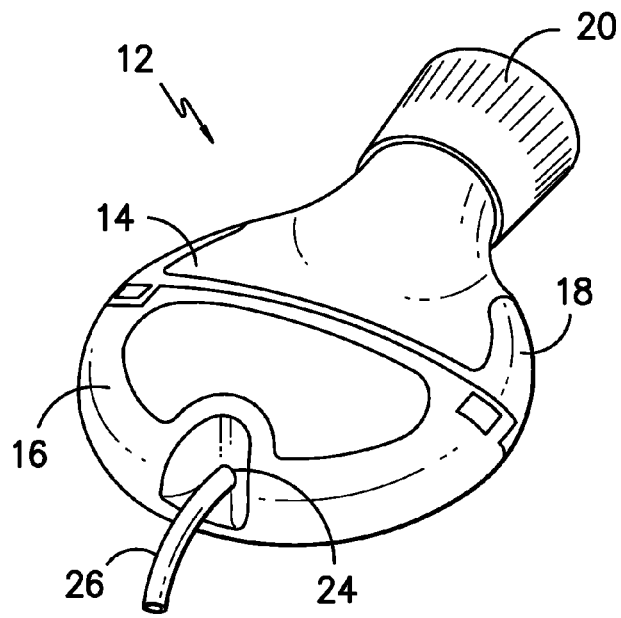
FIG. -3-
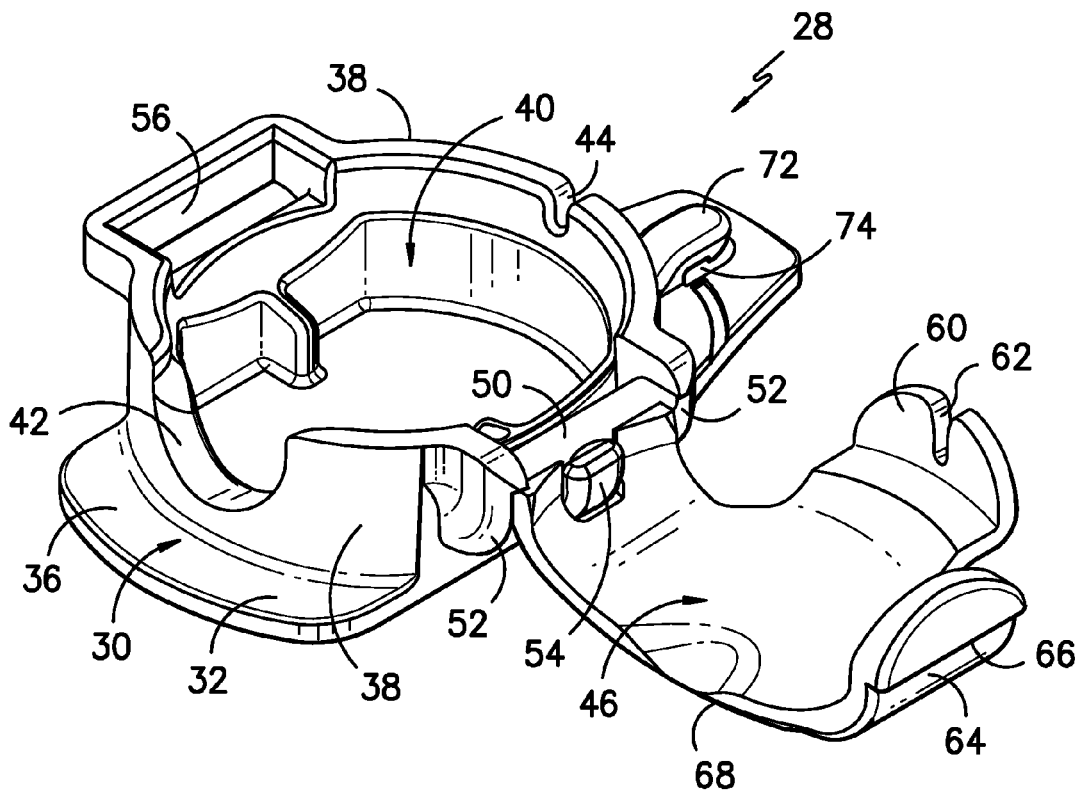
FIG. -4-

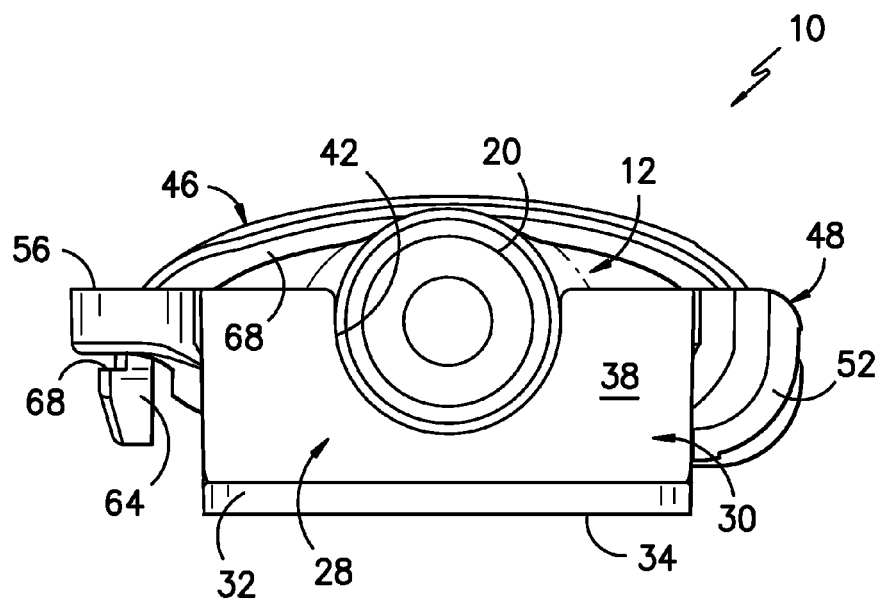
FIG. -5-
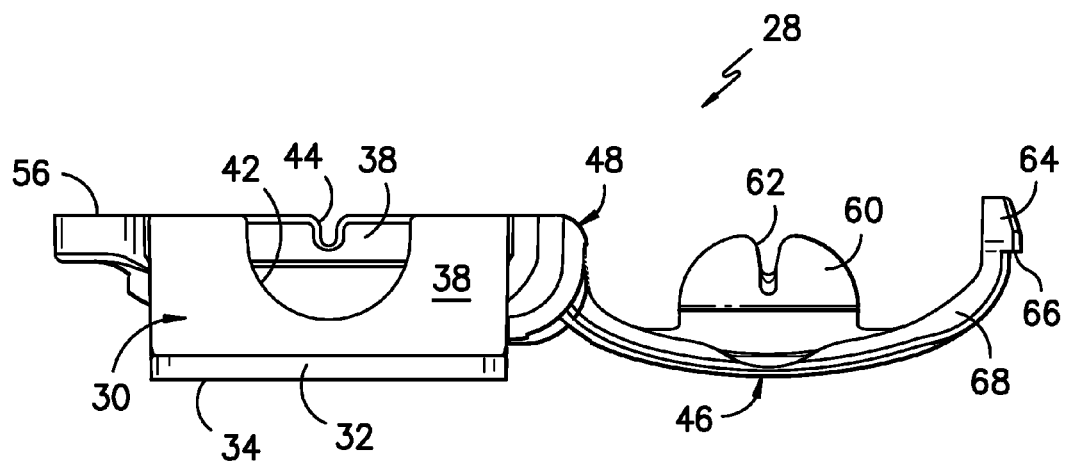
FIG. -6-

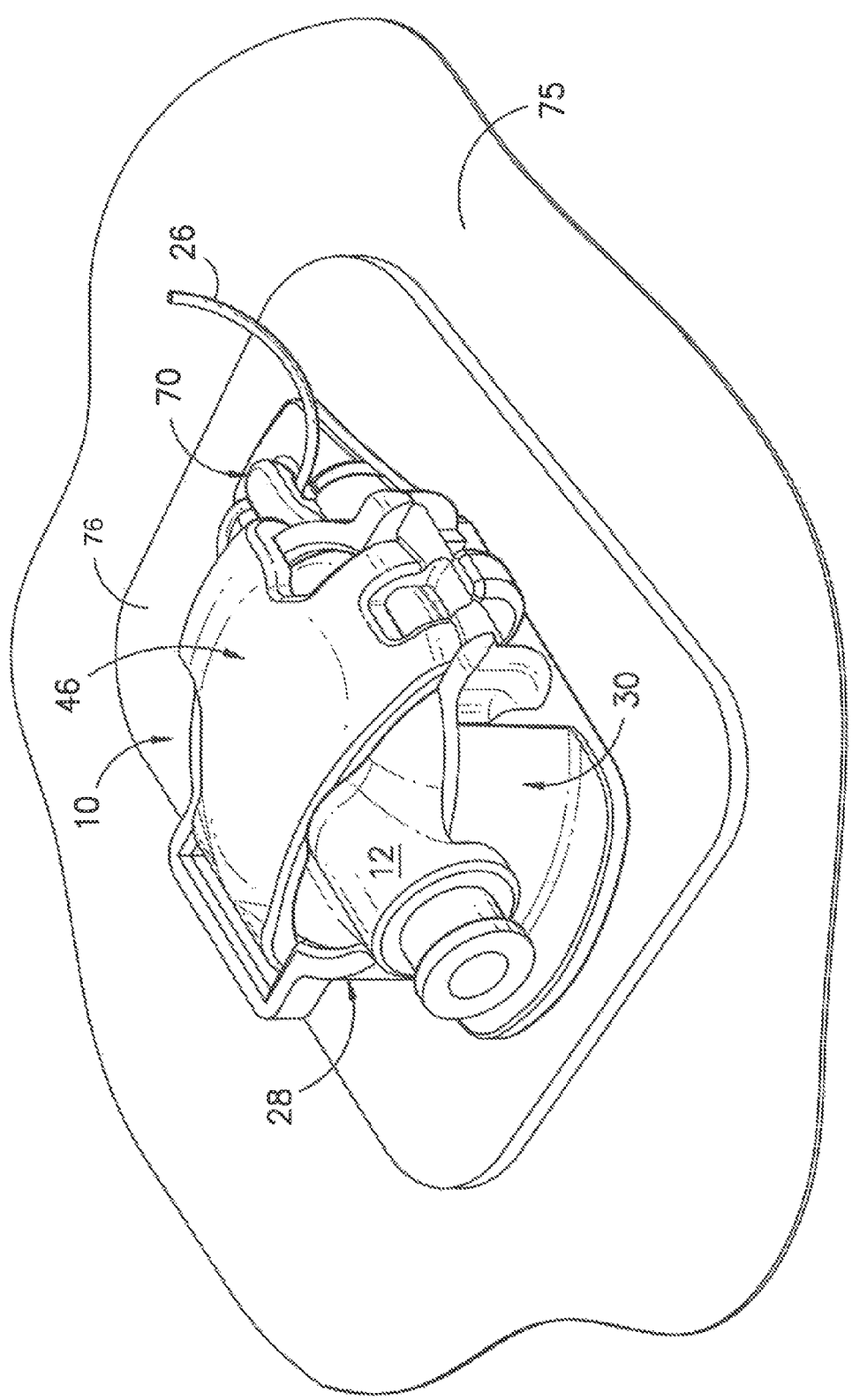
FIG. -7-

CATHETER CONNECTOR SECUREMENT DEVICE

FIELD OF THE INVENTION

The present invention relates generally to the field of medical catheters, and more particularly to a securement device for a catheter connector.

BACKGROUND

The use of catheters to deliver or withdrawn fluids from a patient for various medical procedures is well known. For example, U.S. Pat. No. 7,959,623 describes a pain management system that uses various embodiments of infusion catheters to deliver fluid medication from a pump, through tubing, to a wound site. With such systems, catheter connectors are typically used to connect the catheter to various devices, such as tubing, a fluid reservoir or other fluid delivery device, and so forth. In the system of the '623 patent, a conventional Toughy Borst connector is used to connect the distal end of a medical tube to the proximal end of the catheter.

In addition to Toughy Borst connectors, various other configurations of catheter connectors are available. For example, Epimed International of Farmers Branch, Tex., USA, manufactures a low profile twist-lock catheter connector known as the "Stingray™ Connector." This device has axially aligned halves that twist to an open position to allow insertion of the catheter in a first half, and subsequently twist to a closed position with and audible and tactile click that indicates complete engagement with the catheter. The second half connects to a tube or other fluid delivery device for delivering fluid through the connector to the catheter.

Smiths Medical International Ltd. of the United Kingdom offers a catheter connector under the "EpiFuse™" tradename that consists of two halves joined by a living hinge. A catheter is inserted into a hole at the base of the connector and is retained when the two halves are folded and locked together.

Often, the use of such catheters and connectors must be maintained over extended treatment time periods. It has been a well-known practice to secure these devices with tape. However, the use of a tape dressing can be problematic in that, among other drawbacks, such dressings must be frequently changed, which can irritate the skin around the wound site and lead to build up of adhesive on the catheter devices. This adhesive can result in contaminates adhering to the devices, and can render the devices difficult to handle.

In this regard, devices have been developed to secure a catheter or catheter connector to the patient without excessive use of tape. One such device is the "Grip-Lok™" securement device from Zefon International Inc. of Ocala, Fla., USA. This device includes an adhesive base layer that attaches to the patient's skin. The catheter or catheter/connector combination is pressed onto an adhesive pad attached to an upper surface of the base layer. A Velcro™ closure layer is then folded over the catheter and attaches to the upper surface of the base layer.

Another known catheter connector securement device is the "Statlock™" device from Bard Access Systems of Salt Lake City, Utah, USA. This device includes an anterior anchor pad that attaches to the patient's skin. A "roll-in, roll-out" cage-like structure is attached to an upper surface of the anchor pad and is specifically designed for insertion and retention of a "SnapLock™" catheter connector (also from Bard Access Systems). A separate exit site pad includes a device for securing and preventing migration of the catheter.

U.S. Pat. No. 7,635,355 describes a device for securing a catheter connector on the patient's body. The device includes an anchor pad that attaches to the patient's skin, with a retainer attached to an upper surface of the pad. The retainer has a base member and a cover hinged to the base member and movable between an open and latch-closed position. The base and cover each have respective grooves that cooperate to form a channel in the closed position of the cover. The connector has an elongated body that is received in the channel, whereby axial motion of the connector is inhibited by engagement of the connector within the closed retainer.

The medical art is thus continuously seeking new and improved devices for securing catheters and catheter/connector combinations relative to a patient for extended periods of time without discomfort to the patient, yet which allow for relatively easy release of the catheter or connector. The present invention provides such a device.

SUMMARY OF THE INVENTION

Objects and advantages of the invention will be set forth in part in the following description, or may be obvious from the description, or may be learned through practice of the invention.

In certain aspects, the present invention relates to a catheter connector and securement device system. A component of this system is a connector having a body with a proximal end port configured for mating communication with a fluid delivery device, such as a pump, reservoir, syringe, or the like. This port may have any conventional configuration, such as a Luer lock fitting. A passage is defined in the distal end of the connector body and is sized for sliding receipt of a catheter inserted therein. It should be appreciated that the system is not limited to any particular type, shape, or configuration of catheter connector, and that any number of conventional or commercially available connectors can be used in the system.

The system also includes a securement device having a lower shell member. This lower shell member includes a perimeter wall defining an interior cradle space that conforms to the connector body, with the connector body seated within the cradle space such that the perimeter wall circumferentially engages around the connector body. For example, if the connector has an oval body, the cradle space has a conforming oval shape, and so forth. The perimeter wall has a proximal end groove defined therein, with the connector port extending axially through the groove and beyond the perimeter wall for mating connection with the fluid delivery source. The perimeter wall extends continuously around a distal end of the connector body and has a slot defined therein that is axially aligned with the distal end passage of the connector body, wherein a catheter inserted into the passage resides in the slot where it passes through the perimeter wall.

A cover member is hinged to the lower shell member at a hinge line and is movable from an open position (for insertion and removal of the connector) to a closed position wherein the cover member releasably latches to the lower shell member to retain the connector within the lower shell member.

In certain embodiments, the perimeter wall is a continuous circumferential member that continuously engages around and against the connector body. The port may also continuously engage against the proximal end groove.

It should be appreciated that the cover member may be variously configured. In one embodiment, the cover member has a distal end with a first lip that extends over the perimeter wall in the closed position of the cover member. This first lip has a slot defined therein that axially aligns with the slot in the perimeter wall so that the cover member can be closed over a catheter inserted into the connector.

The cover member may include a second lip that also extends over the perimeter wall in the closed position of the cover member, with the second lip releasably latching into a latch slot extending outwardly from the perimeter wall. This second lip may be disposed opposite from the hinge line, with the cover member having a proximal-most edge that extends between the hinge line and the second lip such that a proximal portion of the perimeter wall and a proximal portion of the connector body are exposed and not covered by the cover member in the closed position of the cover member. This configuration provides an exposed edge that enables relatively easy manual manipulation of the cover member, particularly when opening the cover member. With this configuration, the cover member has a T-shape with points of contact with the perimeter wall at the hinge line, the first lip, and the second lip.

In an alternate embodiment, the cover member may have a continuous lip that circumferentially extends from the catheter slot to the latch, such that the cover member has a generally half-clam shell configuration.

In certain embodiments, a bottom plate of the lower shell member includes a catheter retention device spaced from the slot in the perimeter wall to hold and retain the catheter at a location spaced from the perimeter wall. This retention device may be any suitable mechanism for grasping the catheter without pinching off flow through the catheter. For example, the retention device may be an upstanding biased arm that defines an undercut for receipt of the catheter beneath the arm.

Embodiments of the securement device may include an attachment pad adhered or otherwise connected to the lower surface of the lower shell member, with the attachment pad having an adhesive lower surface for attachment to a patient's skin. This pad serves to position the system directly on the patient at a desired site, for example adjacent to a catheter entry site on the patient.

The present invention also encompasses various embodiments of a securement device for securing a catheter connector to a patient as a stand-alone component (e.g., without a connector seated within the cradle space). Various embodiments of such a securement device are discussed above and set forth in greater detail below.

BRIEF DESCRIPTION OF THE DRAWINGS

FIG. 1 is a perspective view of an exemplary catheter connector and securement device system in accordance with aspects of the invention;

FIG. 2 is an alternate perspective view of the system of FIG. 1;

FIG. 3 is a perspective view of a conventional prior art catheter connector that is used in the system of FIGS. 1 and 2;

FIG. 4 is a perspective view of an embodiment of a securement device in accordance with aspects of the invention;

FIG. 5 is a proximal end view of the system of FIGS. 1 and 2;

FIG. 6 is a distal end view of the securement device of FIG. 4; and

FIG. 7 is a perspective view of the system of FIG. 2 with an attachment pad and catheter.

DETAILED DESCRIPTION OF THE INVENTION

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

The positional terms "proximal" and "distal" are used herein to orient the various components relative to each other and to the patient. "Distal" refers to the direction that is closest to the wound site (e.g., the distal end of the connector is the end oriented towards a catheter insertion site), and "proximal" refers to the opposite direction (e.g., the proximal end of the catheter is inserted into the distal end of the connector).

FIGS. 1 and 2 are perspective views of an embodiment of a system 10 in accordance with aspects of the invention. The system 10 includes a catheter connector, generally 12, seated within a securement device 28. The particular connector 12 illustrated in FIGS. 1 and 2 is the prior art twist-lock Stingray™ connector from Epimed International depicted in FIG. 3 and discussed above in the Background section of the application. This particular connector 12 includes a body 14 having a first half 16 and a second half 18. A proximal end port 20 is configured with the second half 18 and may include any type of conventional fitting for mating communication with a fluid source, such as a syringe, tube, reservoir, pump, and the like. In the illustrated embodiment, the proximal end port 20 includes a conventional Luer lock fitting. The first half 16 of the connector 12 includes a distal end passage 24 having a size for sliding receipt of a catheter 26 inserted therein, as particularly depicted in FIG. 3. As explained above, the Stingray™ connector depicted in FIG. 3 is a twist-lock device wherein the respective halves 16, 18 twist to an open position to allow insertion of the catheter 26 into the distal end passage 24. The halves 16, 18 subsequently twist back into an aligned configuration as depicted in FIG. 3 with an audible and tactile click that indicates complete engagement with the catheter 26.

It should be appreciated that the Stingray™ connector depicted in the various figures is for illustrative purposes only. The system 10, and particularly the securement device 28, is not limited to the Stingray™ connector. Any conventional catheter connector may be utilized in the system 10 in accordance with aspects of the invention, with the securement device 28 configured for receipt of the particular type of connector, as explained in greater detail below.

Referring to the various figures in general, the securement device 28 includes a lower shell member 30. In the illustrated embodiment, the lower shell member 30 has a generally trapezoidal configuration. However, this is for illustrative purposes only. The lower shell member 30 may have a rectangular, oval, square, or any other type of overall shape and configuration. The lower shell member 30 includes a perimeter wall 38 that extends from a bottom surface or plate 32, with the plate 32 having a lower surface 34. The perimeter wall 38 defines an interior cradle space 40 designed to essentially correspond to the outer circumferential shape of the connector 12 seated within the cradle space 40, as can be appreciated particularly from FIGS. 1 and 2. For example, in the depicted embodiment, the cradle space 40 has a generally circular configuration so as to conform to the circular shape of the Stingray™ connector 12 depicted in FIG. 3. If the connector 12 were to have an oval or rectangular shape, then the cradle space 40 would have a correspondingly shaped interior.

Referring to FIGS. 1 and 2 in particular, the perimeter wall 38 circumferentially engages around the connector body 14 so as to form a relatively snug housing for the connector body 14. In the illustrated embodiment, the perimeter wall 38 essentially engages completely around the connector body 14 in that there are no spaces or gaps in the perimeter wall 38. In other embodiments not depicted in the figures, the perimeter wall 38 may have spaces or gaps so long as the connector body 14 is engaged around the circumference thereof at a sufficient number of locations to define a snug cradle for the connector 12.

The perimeter wall 38 includes a proximal end groove 42 defined therein. This groove 42 has a shape and depth so as to accommodate the proximal end port 20 of the connector 12. In other words, the proximal end port 20 is seated within the proximal end groove 42 at the location where the port 20 extends through the perimeter wall 38. As particularly seen in FIGS. 5 and 6, the groove 42 may engage essentially completely against the proximal end port 20 from one end of the groove to the other.

It should be appreciated that with the relatively snug cradle provided by the cradle space 40 engaging against the connector body 14, as well as the groove 42 engaging against the proximal end port 20, the connector 12 is securely and firmly seated within the securement device 28 so that there is little or no relative movement between the components.

At its distal end, the perimeter wall 38 may extend continuously around the distal end of the connector body 14. A slot 44 is defined in the upper surface of the perimeter wall 38 at the distal end and axially aligns with the distal end passage 24 in the connector body 14. In this manner, a catheter 26 inserted into the passage 24 resides in the slot 44 where the catheter 26 passes through the perimeter wall 38, as can be readily appreciated from the views of FIG. 6 and FIG. 7.

Referring again to the figures in general, the securement device 28 includes a cover member 46 that is hinged to the lower shell member 30 at a hinge line 48. The cover member 46 is moveable from an open position depicted in FIGS. 4 and 6 to the closed position depicted in FIGS. 1, 2, and 5. In the open position, the cradle space 40 is accessible for insertion of the connector 12. In particular, the body 14 of the connector 12 can be pressed into the cradle space 40 with the port 20 extending through the groove 42 and the distal end passage 24 aligned with the slot 44. The cover member 46 is moveable to the closed position depicted in FIG. 1 and latches to the lower shell member 30 by means of any suitable latch device. In the embodiment depicted in the figures, the latch device includes a latch slot 56 defined in the lower shell member 30 that is engaged by an overhanging lip 64 on the cover member 46. The lip 64 is biased and flexible to a degree necessary for a shoulder 66 on the lip 64 to slide through the slot 56, wherein the lip 64 flexes outwardly and the shoulder 66 engages against the underside of the slot 56, as can be appreciated from FIGS. 5 and 6. It should be understood, however, that any suitable mechanical latch device may be used to secure the cover member 46 relative to the lower shell member 30.

Similarly, the system 10 is not limited to any particular hinge mechanism between the cover member 46 and the lower shell member 30. In the embodiment illustrated in the figures, the hinge line 48 is defined by a rod 50 on the cover member 46 that engages between flanges 52 formed on the lower shell member 30. The rod 50 is also seated within a biased support 54 that supports the rod 50 for rotation and ensures that the rod 50 is maintained engaged between the flanges 52. Again, any suitable hinge mechanism may be used in this regard, including a living hinge.

It should further be appreciated that the cover member 46 may be variously configured within the scope and spirit of the invention. In the illustrated embodiment, the cover member 46 has a distal end with an overhanging first lip 60 that extends over the perimeter wall 38 in the closed position of the cover member 46, as particularly illustrated in FIG. 1. This lip 60 has a slot 62 defined therein that aligns with the slot 44 in the perimeter wall 38 in the closed position of the cover member 46. With this configuration, the cover member 46 can be closed with a catheter 26 inserted into the passage 24 in the connector body 14, with the first lip 60 and slot 62 engaging around the catheter.

Referring particularly to FIG. 4, the latch lip 64 with the shoulder 66 may be disposed directly opposite from the hinge line 48, with the cover member 46 having a proximal-most edge 68 that extends between the hinge line 48 and second lip 64. With this configuration, as particularly seen in FIG. 2, a proximal portion of the connector body 14 and the perimeter wall 38 are exposed even when the cover member 46 is in the closed position. This edge 68 provides a location for relatively easy manual manipulation of the cover member 46, particularly when opening the cover member from the closed position. In the embodiment illustrated, the cover member 46 has a generally T-shaped configuration with points of contact with the perimeter wall 38 at the hinge line 48, the first lip 60, and the second lip 64.

In an alternate embodiment not depicted in the figures, the cover member 46 may have a continuous circumferential lip so as to engage essentially completely around the perimeter wall 38. In this embodiment, a corresponding groove would be defined in the continuous lip to conform over the proximal end port 20 in the connector 12. Instill another embodiment, the cover member 46 may have a generally half-clam shell configuration with a continuous lip.

Referring particular to FIGS. 1, 2, and 7, certain embodiments of the securement device 28 may include a catheter retention device 70 spaced from the perimeter wall 38. For example, this retention device 70 may be defined by a flexible or biased projection or other arm-type structure 72 angled upwardly and away from the bottom plate 32 of the securement device 28. The projection 72 defines an undercut 74 having a height for frictional engagement with a catheter 26 pressed under the projection 72. This catheter retention device 70 provides an alternate location for securement of the catheter 26 relative to the securement device 28 and, thus, prevents inadvertent removal or pulling of the catheter 26 from the connector 12.

Referring to FIG. 7, an embodiment of the system 10 in accordance with aspects of the invention may include an attachment pad 76, for example a foam pad, for adhering the system 10 to a patient, for example directly to the patient's skin 75 adjacent to a catheter insertion site. This pad 76 may be made of any suitable material and may be adhered to the lower surface 34 of the bottom plate member 32. The bottom surface of the pad 76 may include any suitable medical grade adhesive covered by a release layer, as is understood by those skilled in the art.

It should be further appreciated that aspects of the present invention also encompass various embodiments of the securement device 28 as a stand-alone component (e.g., without a connector 12 seated within the cradle space 40 of the securement device 28). In this regard, the discussion set forth above of the securement device 28 is relevant to the stand-alone securement device in accordance with aspects of the invention.

While the present invention has been described in connection with certain preferred embodiments it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:

1. A catheter connector and securement device system, comprising:
    a connector, said connector further comprising:
        a body having a proximal end port configured thereon for mating communication with a fluid delivery device;
        said body having a distal end passage defined therein axially aligned with said port, said passage having a size for receipt of a catheter inserted therein;
    a securement device, said securement device further comprising:
        a lower shell member;
        said lower shell member having a perimeter wall defining an interior cradle space that conforms to a shape of said connector body, said connector body seated within said cradle space such that said perimeter wall continuously circumferentially engages around said connector body, said passage in said connector body located within an interior of said perimeter wall;
        said perimeter wall having a proximal end groove defined therein, said port extending axially through said groove and beyond said perimeter wall;
        said perimeter wall extending continuously around a distal end of said connector body such that said distal end of said connector body is completely within said interior cradle space, said perimeter wall having a slot defined therein that is axially aligned with said distal end passage, wherein a catheter inserted into said passage is directly seated within said slot and passes through said perimeter wall; and
        a cover member hinged to said lower shell member at a hinge line and movable from an open position for insertion and removal of said connector to a closed position wherein said cover member releasably latches to said lower shell member to retain said connector within said lower shell member.

2. The system as in claim 1, wherein said groove continuously engages against said port.

3. The system as in claim 1, wherein said cover member has a distal end with a first lip that extends over said perimeter wall in the closed position of said cover member, said lip having a slot defined therein that axially aligns with said slot in said perimeter wall.

4. The system as in claim 3, wherein said cover member comprises a second lip that extends over said perimeter wall in the closed position of said cover member, said second lip releasably latching into a latch slot extending from said perimeter wall, said second lip disposed opposite from said hinge line, said cover member having a proximal-most edge extending between said hinge line and said second lip such that a proximal portion of said perimeter wall is exposed and not covered by said cover member in said closed position of said cover member.

5. The system as in claim 4, wherein said cover member has a T-shape configuration with points of contact with said perimeter wall at said hinge line, said first lip, and said second lip.

6. The system as in claim 1, wherein said lower shell member further comprises a catheter retention device spaced from said slot in said perimeter wall, said retention device upstanding arm that an undercut area between a bottom plate of said lower shell upstanding arm for receipt of the catheter in said undercut area.

7. The system as in claim 1, wherein said securement device further comprises an attachment pad connected to a lower surface of lower shell member, said attachment pad having an adhesive lower surface for attachment to a patient's skin.

8. The system as in claim 1, wherein said securement device is a rigid molded component.

9. A securement device for securing a catheter connector to a patient, wherein the connector has a body with a proximal end having a port configured thereon for communication with a fluid delivery device, and a distal end with a passage defined therein axially aligned with the port and having a size for receipt of a catheter inserted therein, said securement device comprising:
    a lower shell member;
    said lower shell member having a perimeter wall defining an interior cradle space for receipt of the connector body such that said perimeter wall continuously circumferentially engages around the connector body;
    said perimeter wall having a proximal end with a groove defined therein for passage of the connector port axially beyond said perimeter wall through said groove;
    said perimeter wall having a distal end configured to completely encircle the distal end of the connector body within said interior cradle space, said distal end of said perimeter wall having a slot defined therein that axially aligns with the passage in the connector so that a catheter inserted in the passage is directly seated within said slot and passes through said perimeter wall; and
    a cover member hinged to said lower shell member at a hinge line and movable from an open position for insertion and removal of the connector to a closed position wherein said cover member releasably latches to said lower shell member to retain the connector within said lower shell member.

10. The securement device as in claim 9, wherein said groove is shaped so as to continuously engage against the connector port when the connector is seated within said cradle space.

11. The securement device as in claim 9, wherein said cover member has a distal end with a first lip that extends over said perimeter wall in the closed position of said cover member, said lip having a slot defined therein that axially aligns with said slot in said perimeter wall.

12. The securement device as in claim 11, wherein said cover member comprises a second lip that extends over said perimeter wall in the closed position of said cover member, said second lip releasably latching into a latch slot extending from said perimeter wall, said second lip disposed opposite from said hinge line, said cover member having a proximal-most edge extending between said hinge line and said second lip such that a proximal portion of said perimeter wall is exposed and not covered by said cover member in said closed position of said cover member.

13. The securement device as in claim 12, wherein said cover member has a T-shape configuration with points of contact with said perimeter wall at said hinge line, said first lip, and said second lip.

14. The securement device as in claim 9, wherein said lower shell member further comprises a catheter retention device spaced from said slot in said perimeter wall, said retention device comprising an upstanding arm that defines an undercut area between a bottom plate of said lower shell member and said upstanding arm for receipt of the catheter in said undercut area.

15. The securement device as in claim 9, wherein said securement device further comprises an attachment pad connected to a lower surface of said lower shell member, said attachment pad having an adhesive lower surface for attachment to a patient's skin.

16. The securement device as in claim 9, wherein said securement device is a rigid molded component.

* * * * *